(12) United States Patent
Krähmer et al.

(10) Patent No.: US 6,569,805 B1
(45) Date of Patent: May 27, 2003

(54) HERBICIDAL COMPOSITIONS

(75) Inventors: Hansjörg Krähmer, Hofheim (DE); Thomas Auler, Bad Soden (DE); Christopher Rosinger, Hofheim (DE); Heinz Hagemeister, Düsseldorf (DE); David Drexler, Kelkheim (DE)

(73) Assignee: Aventis CropScience GmbH, Frankfurt (DE)

( * ) Notice: Subject to any disclaimer, the term of this patent is extended or adjusted under 35 U.S.C. 154(b) by 0 days.

(21) Appl. No.: 09/694,869

(22) Filed: Oct. 24, 2000

(30) Foreign Application Priority Data

Oct. 26, 1999 (DE) .......................... 199 51 426

(51) Int. Cl.⁷ .................. A01N 25/02; A01N 47/36
(52) U.S. Cl. .................. 504/103; 504/106; 504/214; 504/362
(58) Field of Search .................. 504/214, 103, 504/106, 362

(56) References Cited

U.S. PATENT DOCUMENTS

| | | | |
|---|---|---|---|
| 5,104,443 A | 4/1992 | Kehne et al. .................. 71/92 |
| 5,411,932 A | * 5/1995 | Yoshida et al. .............. 504/132 |
| 5,518,991 A | 5/1996 | Frisch et al. ................ 504/138 |
| 5,731,264 A | * 3/1998 | Narayanan et al. ......... 504/116 |
| 5,922,646 A | 7/1999 | Schnabel et al. ............ 504/214 |

FOREIGN PATENT DOCUMENTS

| | | |
|---|---|---|
| EP | 0 007 687 A1 | 2/1980 |
| EP | 0 030 138 A1 | 6/1981 |
| EP | 0 313 317 | 4/1989 |
| EP | 0 598 515 | 5/1994 |
| WO | WO 94/24858 | 11/1994 |
| WO | WO 98/16102 | 4/1998 |
| WO | WO 00/25586 | 5/2000 |
| WO | WO 00/44226 | 8/2000 |
| WO | WO 00/44227 | 8/2000 |

OTHER PUBLICATIONS

AN 1997–347334, also referred to as XP 002161182 Abst of JP 9–143006, Jun. 1997.
CA 128:240725, Abst. of JP 10–59809, Mar. 1998.
CPR T&0R 1999 Supplement, pp. 55–56.

* cited by examiner

Primary Examiner—S. Mark Clardy
(74) Attorney, Agent, or Firm—Frommer Lawrence & Haug LLP

(57) ABSTRACT

The present invention relates to a herbicidal composition comprising

A) one or more sulfonylureas of the formula (I) and/or their salts

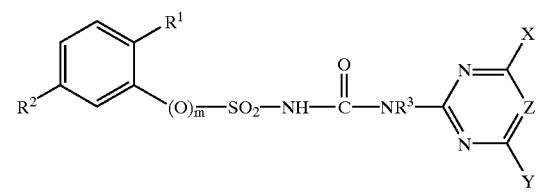

(I)

in which
$R^1$ is $C_2$–$C_4$-alkoxy or CO—$R^a$, where $R^a$ equals OH, $C_1$–$C_4$-alkoxy or $NR^bR^c$, in which $R^b$ and $R^c$ independently of one another are identical or different and are H or $C_1$–$C_4$-alkyl,
$R^2$ is halogen or $(A)_n$—$NR^dR^e$, in which n equals zero or 1, A is a group CR'R", in which R' and R" independently of one another are identical or different and are H or $C_1$–$C_4$-alkyl, $R^d$ equals H or $C_1$–$C_4$-alkyl and $R^e$ is an acyl radical and, in the event that $R^1$ equals $C_2$–$C_4$-alkoxy, $R^e$ may also be H,
$R^3$ is H or $C_1$–$C_4$-alkyl,
m equals zero or 1,
X and Y independently of one another are identical or different and are $C_1$–$C_6$-alkyl, $C_1$–$C_6$-alkoxy or $C_1$–$C_6$-alkylthio, each of the three radicals mentioned being unsubstituted or substituted by one or more radicals selected from the group consisting of halogen, $C_1$–$C_4$-alkoxy and $C_1$–$C_4$-alkylthio, or are $C_3$–$C_6$-cycloalkyl, $C_2$–$C_6$-alkenyl, $C_2$–$C_6$-alkynyl, $C_3$–$C_6$-alkenyloxy or $C_3$–$C_6$-alkynyloxy, preferably $C_1$–$C_4$-alkyl or $C_1$–$C_4$-alkoxy,
Z equals CH or N, and
B) one or more vegetable oils.

7 Claims, No Drawings

HERBICIDAL COMPOSITIONS

The invention lies in the technical field of the crop protection products; in particular, the invention relates to herbicidal compositions comprising certain phenylsulfonylureas and/or their salts and vegetable oils which are outstandingly suitable for controlling harmful plants in crops.

The use of sulfonylureas as active component of crop protection products is known (for example EP-A-007 687, EP-A-030 138). Likewise, it is known to combine sulfonylureas such as Nicosulfuron (Accent®) with vegetable oils (for example CPR/T & OR 1999 Adjuvant Reference Supplement-C&P Press 1998, p. 55/56).

The object of the present invention was to provide herbicidal compositions which exhibit a particularly high herbicidal activity, selective properties toward agricultural crop plants and also a high crop plant tolerance.

Surprisingly, it has now been found that this object is achieved by herbicidal compositions which comprise specific sulfonylureas in combination with vegetable oils.

The present invention thus relates to herbicidal compositions comprising

A) one or more sulfonylureas of the formula (I) and/or their salts

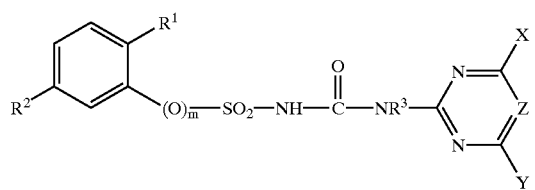

(I)

in which
$R^1$ is $C_2$–$C_4$-alkoxy or CO—$R^a$, where $R^a$ equals OH, $C_1$–$C_4$-alkoxy or $NR^bR^c$, in which $R^b$ and $R^c$ independently of one another are identical or different and are H or $C_1$–$C_4$-alkyl, $R^2$ is halogen or $(A)_n$—$NR^dR^e$, in which n equals zero or 1, A is a group CR'R'', in which R' and R'' independently of one another are identical or different and are H or $C_1$–$C_4$-alkyl, $R^d$ equals H or $C_1$–$C_4$-alkyl and $R^e$ is an acyl radical and, in the event that $R^1$ equals $C_2$–$C_4$-alkoxy, $R^2$ may also be H, $R^3$ is H or $C_1$–$C_4$-alkyl, m equals zero or 1, preferably zero, X and Y independently of one another are identical or different and are $C_1$–$C_6$-alkyl, $C_1$–$C_6$-alkoxy or $C_1$–$C_6$-alkylthio, each of the three radicals mentioned being unsubstituted or substituted by one or more radicals selected from the group consisting of halogen, $C_1$–$C_4$-alkoxy and $C_1$–$C_4$-alkylthio, or are $C_3$–$C_6$-cycloalkyl, $C_2$–$C_6$-alkenyl, $C_2$–$C_6$-alkynyl, $C_3$–$C_6$-alkenyloxy or $C_3$–$C_6$-alkynyloxy, preferably $C_1$–$C_4$-alkyl or $C_1$–$C_4$-alkoxy, Z equals CH or N, and B) one or more vegetable oils.

The compounds of the formula (I) can form salts in which the hydrogen of the —$SO_2$—NH— group is replaced by an agriculturally suitable cation. Examples of these salts are metal salts, in particular alkali metal salts (for example sodium or potassium salts) or alkaline-earth metal salts, or else ammonium salts or salts with organic amines. Equally, salt formation can take place by subjecting a strong acid to an addition reaction with the heterocyclic moiety of the compounds of the formula (I). Suitable examples are HCl, $HNO_3$, trichloroacetic acid, acetic acid or palwithic acid. Especially advantageous compounds are those in which the salt of the herbicide of the formula (I) is formed by replacing the hydrogen of the —$SO_2$—NH— group by a cation selected from the group consisting of the alkali metals, alkaline-earth metals and ammonium, preferably sodium.

As long as the compounds of the formula (I) contain one or more asymmetric carbon atoms or else double bonds which are not specifically mentioned in the formula, they are still encompassed by the formula (I). The stereoisomers which are possible and which are defined by their specific spatial shape, such as enantiomers, diastereoisomers, Z- and E-isomers, are all encompassed by the formula (I) and can be obtained by customary methods from mixtures of the stereoisomers or else prepared by stereoselective reactions in combination with the use of stereochemically pure starting materials. The abovementioned stereoisomers in pure form and also their mixtures can thus be employed in accordance with the invention.

An acyl radical for the purposes of the present description means the radical of an organic acid which is formed formally by eliminating an OH group from the organic acid, for example the radical of a carboxylic acid and radicals of acids derived therefrom such as thiocarboxylic acid, optionally N-substituted iminocarboxylic acids or the radicals of carbonic monoesters, optionally N-substituted carbamic acids, sulfonic acids, sulfinic acids, phosphonic acids, phosphinic acids.

An acyl radical is preferably formyl or acyl selected from the group consisting of CO—$R^X$, CS—$R^X$, CO—$OR^X$, CS—$OR^X$, CS—$SR^X$, $SOR^Y$ or $SO_2R^Y$, where $R^X$ and $R^Y$ are in each case a $C_1$–$C_{10}$-hydrocarbon radical such as $C_1$–$C_{10}$-alkyl or $C_6$–$C_{10}$-aryl which is unsubstituted or substituted, for example by one or more substituents selected from the group consisting of halogen such as F, Cl, Br, I, alkoxy, haloalkoxy, hydroxyl, amino, nitro, cyano or alkylthio, or $R^X$ and $R^Y$ are aminocarbonyl, or aminosulfonyl, the two last-mentioned radicals being unsubstituted, N-monosubstituted or N,N-disubstituted, for example by substituents selected from the group consisting of alkyl or aryl.

Acyl is, for example, formyl, haloalkylcarbonyl, alkylcarbonyl such as ($C_1$–$C_4$)alkylcarbonyl, phenylcarbonyl, it being possible for the phenyl ring to be substituted, or is alkyloxycarbonyl, such as ($C_1$–$C_4$) alkyloxycarbonyl, phenyloxycarbonyl, benzyloxycarbonyl, alkylsulfonyl, such as ($C_1$–$C_4$) alkylsulfonyl, alkylsulfinyl, such as $C_1$–$C_4$ (alkylsulfinyl), N-alkyl-1-iminoalkyl, such as N-($C_1$–$C_4$)-1-imino-($C_1$–$C_4$)alkyl and other radicals of organic acids. For the purposes of the present description, the radicals alkyl and alkyl-containing radicals such as alkoxy and alkylthio and the corresponding unsubstituted and/or substituted radicals in the carbon skeleton are in each case straight-chain or branched. Unless otherwise specified, the lower carbon skeletons, for example those having 1 to 4 carbon atoms, are preferred for these radicals. Alkyl radicals, also in the composite meanings such as alkoxy, or alkylthio are, for example, methyl, ethyl, n- or i-propyl, n-, i-, t- or 2-butyl, pentyls, hexyls, such as n-hexyl, i-hexyl and 1,3-dimethylbutyl, heptyls, such as n-heptyls, 1-methylhexyl and 1,4-dimethylpentyl.

While sulfonylureas of the formula (I) and their salts are known in principle (see, for example, EP-A-342 569, EP-A-574 418, EP-A-723 534 and EP-A-757 679, which are expressly referred to herewith), their outstanding suitability as components in combinations in, preferably, synergistic mixtures with vegetable oils cannot be seen from the prior art.

Preferred sulfonylureas are those of the formula (I) and/or their salts in which m equals 1, $R^1$ is $C_2$–$C_4$-alkoxy and $R^2$ equals H.

Likewise preferred sulfonylureas of the formula (I) and/or their salts are those in which m equals 0, and
- a) $R^1$ equals CO—($C_1$–$C_4$-alkoxy) and $R^2$ equals halogen, preferably iodine, or $R^2$ equals $CH_2$—$NHR^e$, in which $R^e$ is an acyl radical, preferably $C_1$–$C_4$-alkylsulfonyl, or
- b) $R^1$ equals CO—N($C_1$–$C_4$-alkyl)$_2$ and $R^2$ equals $NHR^e$, in which $R^e$ is an acyl radical, preferably formyl.

Examples of compounds of the formula (I) and/or their salts which may be mentioned are:

A1=N-(4,6-dimethoxypyrimidin-2-ylaminocarbonyl)-2-methoxycarbonyl-5-acetylaminobenzenesulfonamide A2=N-(4,6-dimethoxypyrimidin-2-ylaminocarbonyl)-2-methoxycarbonyl-5-(N-formyl-N-methylaminomethyl)benzenesulfonamide sodium salt A3=N-(4,6-dimethoxypyrimidin-2-ylaminocarbonyl)-2-methoxycarbonyl-5-acetylamino)benzenesulfonamide sodium salt A4=N-(4,6-dimethoxypyrimidin-2-ylaminocarbonyl2-methoxycarbonyl-5-(N-methyl-N-propionylamino)benzenesulfonamide sodium salt A5=N-(4,6-dimethoxypyrimidin-2-ylaminocarbonyl2-methoxycarbonyl-5-(N-isopropionylmethylamino)benzenesulfonamide sodium salt A6=N-(4,6-dimethoxypyrimidin-2-ylaminocarbonyl2-methoxycarbonyl-5-(N-methoxycarbonylaminomethyl)benzenesulfonamide sodium salt A7=N-(4,6-dimethoxypyrimidin-2-ylaminocarbonyl)-2-(N,N-dimethyl-aminocarbonyl)-5-(N-methoxycarbonylamino)benzenesulfonamide sodium salt A8=N-(4,6-dimethoxypyrimidin-2-ylaminocarbonyl)-2-(N,N-dimethyl-aminocarbonyl)-5-(N-formylamino)benzenesulfonamide (foramsulfuron)

A9=N-(4,6-dimethoxypyrimidin-2-ylaminocarbonyl)-2-(N,N-dimethyl-aminocarbonyl)-5-(N-formylamino)benzenesulfonamide sodium salt (foramsulfuron-sodium)

A10=N-(4,6-dimethoxypyrimidin-2-ylaminocarbonyl)-2-methoxycarbonyl-5-(N-methylsulfonylaminomethyl)benzenesulfonamide sodium salt (mesosulfuron-methyl-sodium)

A11=N-(4,6-dimethoxypyrimidin-2-ylaminocarbonyl)-2-methoxycarbonyl-5-(N-methylsulfonylaminomethyl)benzenesulfonamide (mesosulfuron-methyl)

A12=N-(4,6-dimethoxypyrimidin-2-ylaminocarbonyl)-2-methoxycarbonyl-5-(N-methoxycarbonylaminomethyl)benzenesulfonamide sodium salt A13=1-(4,6-dimethoxypyrimidin-2-yl)-3-(2-ethoxyphenoxysulfonyl)urea (ethoxysulfuron)

A14=1-(4,6-dimethoxypyrimidin-2-yl)-3-(2-ethoxyphenoxysulfonyl)urea sodium salt (ethoxysulfuron sodium)

A15=N-(4-methoxy-6-methyl-1,3,5-triazin-2-ylaminocarbonyl)-2-methoxy-carbonyl-5-iodobenzenesulfonamide (iodosulfuron-methyl)

A16=N-(4-methoxy-6-methyl-1,3,5-triazin-2-ylaminocarbonyl)-2-methoxy-carbonyl-5-iodobenzenesulfonamide sodium salt (iodosulfuron-methyl-sodium)

A17=N-(4,6-dimethoxyprimidin-2-ylaminocarbonyl)-2-methoxycarbonyl-5-(N-methylsulfonyl-N-methylaminomethyl)benzenesulfonamide A18=N-(4,6-dimethoxypyrimidin-2-ylaminocarbonyl)-2-(N,N-dimethyl-aminocarbonyl)-5-(N-propionylamino)benzenesulfonamide sodium salt The term vegetable oils describes, for the purposes of the present invention, oils from oil plants such as soya oil, rapeseed oil, corn oil, sunflower oil, cotton seed oil, linseed oil, coconut oil, palm oil, safflower oil, or castor oil, in particular rapeseed oil, and its transesterification products, for example alkyl esters such as rapeseed oil methyl ester or rapeseed oil ethyl ester.

The vegetable oils are preferably esters of $C_{10}$–$C_{22}$-, preferably $C_{12}$–$C_{20}$-fatty acids. The $C_{10}$–$C_{22}$-fatty acid esters are, for example, esters of unsaturated or saturated $C_{10}$–$C_{22}$-fatty acids, in particular those with an even number of carbon atoms, for example erucic acid, lauric acid, palmitic acid and, in particular, $C_{18}$-fatty acids such as stearic acid, oleic acid, linoleic acid or linolenic acid.

Examples of $C_{10}$–$C_{22}$-fatty acid esters are esters which are obtained by reacting glycerol or glycol with the $C_{10}$–$C_{22}$-fatty acids, as they are found, for example, in oils from oil plants, or $C_1$–$C_{20}$-alkyl-$C_{10}$–$C_{22}$-fatty acid esters, as they can be obtained, for example, by transesterifying the abovementioned glycerol- or glycol-$C_{10}$–$C_{22}$-fatty acid esters with $C_1$–$C_{20}$-alcohols (for example methanol, ethanol, propanol or butanol). The transesterification can be carried out by known methods as they are described, for example, in Römpp Chemie Lexikon, 9th. edition, Volume 2, page 1343, Thieme Verlag Stuttgart.

Preferred $C_1$–$C_{20}$-alkyl-$C_{10}$–$C_{22}$-fatty acid esters are methyl esters, ethyl esters, propyl esters, butyl esters, 2-ethylhexyl esters and dodecyl esters. Preferred glycol- and glycerol-$C_{10}$–$C_{22}$-fatty acid esters are the homogeneous or mixed glycol esters and glycerol esters of $C_{10}$–$C_{22}$-fatty acids, in particular of those fatty acids which have an even number of carbon atoms, for example erucic acid, lauric acid, palmitic acid and, in particular, $C_{18}$-fatty acids such as stearic acid, oleic acid, linoleic acid or linolenic acid.

The herbicidal compositions according to the invention may comprise the vegetable oils, for example in the form of commercially available oil-containing formulation additives, in particular those based on rapeseed oil such as Hasten® (Victorian Chemical Company, Australia, termed Hasten hereinbelow, main constituent: rapeseed oil ethyl ester), Actirob®B (Novance, France, termed Actirob B hereinbelow, main constituent: rapeseed oil methyl ester), Rako-Binol® (Bayer AG, Germany, termed Rako-Binol hereinbelow, main constituent: rapeseed oil), Renol® (Stefes, Germany, termed Renol hereinbelow, vegetable oil constituent: rapeseed oil methyl ester) or Stefes Mero® (Stefes, Germany, termed Mero hereinbelow, main constituent: rapeseed oil methyl ester).

Combinations of the active substances of the formula (I) and/or their salts with vegetable oils have an outstanding herbicidal action and, in a preferred embodiment, superadditive effects. Owing to the improved control of the harmful plants by the herbicidal compositions according to the invention, it becomes possible to lower the application rate and/or increase the safety margin. Both make sense both economically and ecologically. The choice of the quantities of components A+B to be employed and the ratio of the components A:B depend on various factors. Not inconsiderable in this context are, inter alia, the type of components A and B, the developmental stage of the grass weeds or broad-leaved weeds, the weed spectrum to be controlled, environmental factors, climatic conditions, soil conditions and the like.

In a preferred embodiment, herbicidal compositions according to the invention are characterized by a synergistically effective content of a combination of the compounds of the formula (I) and/or their salts (type-A compounds) with vegetable oils B). The herbicidal compositions according to the invention have, as a rule, an inherent synergistic action, even in the case of combinations with application rates or weight ratios of A:B, where a synergism cannot be detected readily in each case—for example because the individual compounds are usually employed in the combination in application rates which are quite different, or else because control of the harmful plants is very good even just with the individual compounds.

The herbicidal compositions according to the invention can be employed pre- or post-emergence, for example by spraying. The use of the herbicidal compositions according to the invention allows the amount of preparation required for controlling the weeds to be reduced considerably.

The application rates of the compound(s) of the formula (I) and/or the salts thereof are generally between 0.1 and 200 g ai/ha (ai=active ingredient, i.e. application rate based on the active substance), preferably between 0.5 and 100 g ai/ha.

The application rates of vegetable oils B) are generally in the range of 0.01–20 kg vegetable oil/ha, preferably between 0.5 and 5 kg vegetable oil/ha.

As mentioned, the weight ratios A:B of the components of the herbicidal compositions according to the invention can vary within wide limits, as can their application rates. A preferred range of the application rate ratios, based on weight, is approximately A:B 1:1 to 1:10 000, preferably 1:10 to approximately 1:5000.

Moreover, the intensity and speed of action can be promoted, for example, by activity-enhancing additives such as organic solvents and wefters. If appropriate, such additives therefore allow the dose of active substance to be reduced further.

The herbicidal compositions according to the invention may exist, for example, as mixed formulations of the two components A and B, for example as oil suspension concentrates which are then applied in the customary manner as a dilution with water, or, preferably, as so-called tank mixes by jointly diluting the components A and B, which have previously been formulated separately, with water. For application, the herbicidal compositions according to the invention are applied in particular as aqueous dilution, for example as aqueous dispersions, aqueous suspensions or aqueous emulsions.

If components A and B are formulated separately, then suitable possibilities of formulating active substance component A are, for example, water-soluble wettable powder (WP) and water-dispersible granules (WDG), and the vegetable oil component B can be formulated, for example, as an emulsifiable concentrate (EC).

The formulation types mentioned are known in principle and are described, for example, in: Winnacker-Küchler, "Chemische Technologie" [Chemical Engineering], volume 7, C. Hauser Verlag Munich, 4th Ed. 1986; Wade van Valkenburg, "Pesticide Formulations", Marcel Dekker N. Y., 1973; K. Martens, "Spray Drying Handbook", 3rd Ed. 1979, G. Goodwin Ltd. London.

The herbicidal compositions according to the invention are expediently applied using auxiliaries and additives conventionally used in crop protection, such as liquid and/or solid carriers, diluents and, if appropriate, surfactants such as stickers, wetters, emusifiers and/or dispersants.

Examples of suitable liquid carriers are aliphatic and aromatic hydrocarbons such as toluene, xylene, or else cyclohexanone, isophorone, dimethyl sulfoxide, dimethylformamide or mineral oil fractions.

Examples of solid carriers which are suitable are minerals such as bentonite, silica gel, talc, kaolin, attapulgite, limestone, and products of vegetable origin, such as meals.

Examples of suitable surfactants are polyethylene alkyl phenyl ether, naphthalenesulfonic acid and its salts, phenolsulfonic acids and their salts, fatty alcohol sulfonates, and substituted benzenesulfonic acids and their salts.

The necessary auxiliaries and additives such as inert materials, surfactants, solvents and further additives are likewise known and are described, for example, in: Watkins, "Handbook of Insecticide Dust Diluents and Carriers", 2nd Ed., Darland Books, Caldweil N. J.; H. v. Olphen Introduction to Clay Colloid Chemistry, 2nd Ed., J. Wiley & Sons, N. Y.; Marsden "Solvents Guide", $2^{nd}$ Ed., Interscience, N. Y. 1963; McCutcheon's "Detergents and Emulsifiers Annual", MC Publ. Corp., Ridgewood N. J.; Sisley and Wood, "Encyclopedia of Surface Active Agents", Chem. Publ. Co. Inc., N. Y. 1964; Schönfeldt, "Grenzflächenaktive Äthylenoxidaddukte" [Surface-active ethylene oxide adducts], Wiss. Verlagsgesellschaft, Stuttgart 1976; Winnacker-Küchler "Chemische Technologie", volume 7, C. Hauser Vedag Munich, 4th Ed. 1986.

Based on these formulations, it is also possible to prepare combinations with other agrochemical active substances such as herbicides, insecticides, fungicides, antidotes or safeners, fertilizers and/or growth regulators, for example in the form of a readymix or a tank mix.

If components A and B are formulated separately, possible formulations for the active substance component A are, for example, water-soluble wettable powders (WP) and water-dispersible granules (WDG).

Wettable powders are preparations which are uniformly dispersible in water and which, in addition to the active substances, also comprise ionic and/or nonionic surfactants (wetters, dispersants), for example polyoxyethylated alkylphenols, polyoxyethylated fatty alcohols and fatty amines, fatty alcohol polyglycol ether sulfates, alkanesulfonates or alkylarylsulfonates, sodium 2,2'-dinaphthylmethane-6,6'-disulfonsate, sodium dibutylnaphthalenesulfonate or else sodium oleoylmethyltaurinate, in addition to a diluent or inert substance.

Granules can be produced either by spraying the active substance, or active substances, onto adsorptive, granulated inert material or by applying active substance concentrates to the surface of carriers such as sand, kaolinites or of granulated inert material, by means of stickers, for example sugars such as pentoses or hexoses, or else mineral oils. As a rule, water-dispersible granules are prepared by the customary methods such as spray drying, fluidized-bed granulation, disk granulation, mixing with high-speed mixers and extrusion without solid inert material. Suitable active substances can also be granulated in the manner which is customary for preparing fertilizer granules, if desired in a mixture with fertilizers.

A possibility of formulating the vegetable oils B) is, for example, emulsifiable concentrates (EC). Emulsifiable concentrates are prepared, for example, by dissolving or emulsifying the vegetable oil in an organic solvent, for example butanol, cyclohexanone, dimethylformamide, xylene or else higher-boiling aromatics or hydrocarbons with addition of one or more ionic and/or nonionic surfactants (emulsifiers). Examples of emulsifiers which can be used are: calcium alkylarylsulfonates such as calcium dodecylbenzene-sulfonate or nonionic emulsifiers such as fatty acid polyglycol esters, alkylaryl polyglycol ethers, fatty alcohol polyglycol ethers, propylene oxide/ethylene oxide condensates (for example block copolymers), alkyl polyethers, sorbitan fatty acid esters, polyoxyethylene sorbitan fatty acid esters or other polyoxyethylenesorbitan esters.

The herbicidal compositions of the present invention are prepared especially advantageously by mixing the compounds of the formula (I) and/or their salts (component A) with one or more vegetable oil components B by the tank-mixing method. To do this, component A, for example in the form of an active substance formulation such as WP or WDG, is mixed with component B, for example in the form of a vegetable oil formulation such as EC and with water, for example by stirring. The sequence in which the individual components are added is arbitrary. Thus, for example, it is possible to first introduce water into a mixing vessel, for example the tank, and to add component A and then component B. It is also possible first to add component B to the water and then component A, or components A and B are added simultaneously to the water.

Components A and B may also be present jointly in a mixed formulation, for example as oil suspension concentrate, which is diluted with water in the customary manner and applied.

Oil suspension concentrates can be prepared for example by wet grinding by means of commercially available bead mills and, if appropriate, addition of surfactants, for example as already mentioned above under the other formulation types, the oil component used being a vegetable oil B).

The amount of the active substances in the various formulations can be varied within wide ranges. For example, the formulations comprise approximately 10 to 95 percent by weight of active substances, approximately 90 to 10 percent by weight of liquid or solid carriers and, if appropriate, up to 20 percent by weight of surface-active substances. In wettable powders, the active substance concentration amounts, for example, to approximately 10 to 95% by weight, the remainder to 100% by weight is composed of customary formulation components. In the case of granules such as dispersible granules, the active substance content depends partly on whether the active compound is in liquid or solid form and on which granulation auxiliaries and fillers are used. As a rule, the content amounts to between 10 and 90% by weight in the case of the water-dispersible granules. In oil suspension concentrates, the active substance content is, as a rule, between 0.1 and 20% by weight, preferably between 0.5 and 10% by weight.

In addition, the abovementioned active substance formulations and vegetable oil formulations comprise in each case the stickers, wetters, dispersants, emulsifiers, penetrants, preservatives, antifreeze agents, solvents, fillers, colorants, carriers, antifoams, evaporation inhibitors, pH regulators and viscosity regulators which are customary in each case.

Owing to the relatively low application rate of the herbicidal compositions according to the invention, they are, as a rule, already well tolerated. In particular, the combinations according to the invention lead to a reduction in the absolute application rate in comparison with the individual application of a herbicidal active substance.

If, if desired, the tolerance and/or selectivity of the herbicidal compositions according to the invention are to be increased further, it may be advantageous to apply them jointly as a mixture or staggered in time one after the other together with safeners or antidotes.

Compounds which are suitable as safeners or antidotes for the herbicidal compositions according to the invention are disclosed, for example, in EP-A-333 131 (ZA-89/1960), EP-A-269 806 (U.S. Pat. No. 4,891,057), EP-A-346 620 (AU-A-89/34951) and the international patent applications PCT/EP 90/01966 (WO-91108202) and PCT/EP 90102020 (WO-911078474) and the literature cited therein or can be prepared by the processes described therein. Other suitable safeners are known from EP-A-94 349 (U.S. Pat. No. 4,902,304), EP-A-191 736 (U.S. Pat. No. 4,881,966) and EP-A-0 492 366 and the literature cited therein.

In a preferred embodiment, the herbicidal compositions of the present invention therefore additionally comprise C) one or more compounds which act as safeners or antidotes.

Especially preferred antidotes or safeners or groups of compounds which are suitable as safeners or antidotes for the above-described herbicidal compositions of the invention are, inter alia:

a) Compounds of the dichlorophenylpyrazoline-3-carboxylic acid type, preferably compounds such as ethyl 1-(2,4-dichlorophenyl)-5-(ethoxycarbonyl)-5-methyl-2-pyrazoline-3-carboxylate (compound C1-1, mefenpyr-diethyl) and related compounds as they are described in the intentional application WO 91/07874 (PCT/EP 90102020);

b) Dichlorophenylpyrazolecarboxylic acid derivatives, preferably compounds such as ethyl 1-(2,4-dichlorophenyl)-5-methylpyrazole-3-carboxylate (compound C1-2), ethyl 1-(2,4-dichlorophenyl)-5-isopropylpyrazole-3-carboxylate (compound C1-3), ethyl 1-(2,4-dichlorophenyl)-5-(1,1-dimethylethyl) pyrazole-3-carboxylate (compound C1-4), ethyl 1-(2,4-dichlorophenyl)-5-phenylpyrazole-3-carboxylate (compound C1-5) and related compounds as are described in EP-A-0 333 131 and EP-A-0 269 806;

c) Compounds of the triazolecarboxylic acid type, preferably compounds such as ethyl 1-(2,4-dichlorophenyl)-5-trichloromethyl-(1H)1,2,4-triazole-3-carboxylate (compound C1-6, fenchlorazole) and related compounds (see EP-A-0 174 562 and EP-A-0 346 620);

d) Compounds of the dichlorobenzyl-2-isoxazoline-3-carboxylic acid type, compounds of the 5-benzyl- or 5-phenyl-2-isoxazoline-3-carboxylic acid type, preferably compounds such as ethyl 5-(2,4-dichlorobenzyl)-2-isoxazoline-3-carboxylate (compound C1-7) or ethyl 5-phenyl-2-isoxazoline-3-carboxylate (compound C1-8) and related compounds as they are described in the international patent application WO 91/08202 (PCT/EP 90/01966);

e) Compounds of the 8-quinolinoxyacetic acid type, preferably compounds such as 1-methylhex-1-yl 5-chloro-8-quinolinoxyacetate (C2-1), 1,3-dimethylbut-1-yl 5-chloro-8-quinolinoxyacetate (C2-2), 4-allyloxybutyl 5-chloro-8-quinolinoxyacetate (C2-3), 1-allyloxyprop-2-yl 5-chloro-8-quinolinoxyacetate (C2-4), ethyl 5-chloro-8-quinolinoxyacetate (C2-5), methyl 5-chloro-8-quinolinoxyacetate (C2-6), allyl 5-chloro-8-quinolinoxyacetate (C2-7), 2-(2-propylideneiminooxy)-1-ethyl 5-chloro-8-quinolinoxyacetate (C2-8), 2-oxoprop-1-yl 5-chloro-8-quinolinoxyacetate (C2-9) and related compounds as they are described in EP-A-0 086 750, EP-A-0 094 349 and EP-A-0 191 736 or EP-A-0 492 366;

f) Compounds of the 5-chloro-8-quinolinoxymalonic acid type, preferably compounds such as diethyl 5-chloro-8-quinolinoxymalonate, diallyl 5-chloro-8-quinolinoxymalonate, methyl ethyl 5-chloro-8-quinolinoxymalonate and related compounds as they have been described and proposed in the German patent application EP-A-0 582 198;

g) Active substances of the type of the phenoxyacetic- or -propionic acid derivates or of the aromatic carboxylic acids, such as, for example, 2,4-dichlorophenoxyacetic acid (and its esters) (2,4-D), 4-chloro-2-methylphenoxypropionic acid (mecoprop), MCPA or 3,6-dichloro-2-methoxybenzoic acid (and its esters) (dicamba);

h) Compounds of the 5,5-diphenyl-2-isoxazoline-3-carboxylic acid type, preferably ethyl 5,5-diphenyl-2-isoxazoline-3-carboxylate (C3-1, isoxadifen-ethyl).

i) Compounds known as safeners, for example for rice, such as fenclorim (=4,6-dichloro-2-phenylpyrimidine, Pesticide Manual, 11th Edition, 1997, pp. 511–512), dimepiperate (=S-(1-methyl-1-phenylethyl) 1-piperidinecarbothioate, Pesticide Manual, 11th Edition, 1997, pp. 404–405), daimuron (=1-(1-methyl-1-phenylethyl)-3-p-tolylurea, Pesticide Manual, 11th Edition, 1997, pp. 330), cumyluron (=3-(2-chlorophenylmethyl)-1-(1-methyl-1-phenylethyl)urea, JP-A-60/087254), methoxyphenone (=3,3'-dimethyl-4-methoxybenzophenone, CSB (=1-bromo-4-(chloromethylsulfonyl)-benzene, CAS Reg. No. 54091-064).

In addition, at least some of the compounds mentioned are described in EP-A-0 640 587, which is herewith referred to for publication purposes.

j) A further important group of compounds which are suitable as safeners and antidotes is disclosed in WO 95107897.

The safeners (antidotes) of the above groups a) to j) reduce or contain phytotoxic effects which may occur in crops of useful plants when employing the herbicidal compositions according to the invention without adversely affecting the efficacy of the herbicides against harmful plants. This allows the field of application of the herbicidal compositions according to the invention to be widened considerably, and, in particular, the use of safeners allows herbicidal compositions to be employed whose use has previously only been possible with limitations or with insufficient success, i.e. combinations which, without safeners, had a poor spectrum of action and led to insufficient control of harmful plants when applied at low dosage rates.

Components A and B of the herbicidal compositions according to the invention and the abovementioned safeners can be applied together (as a readymix or by the tank mix method) or in succession in an arbitrary sequence. The weight ratio of safener:herbicide (compound(s) of the formula (I) and/or the salts thereof, may vary within wide limits and is preferably in the range of 1:100 to 100:1, in particular 1:100 to 50:1. The amounts of herbicide(s) and safener(s) which are optimal in each case depend usually on the type of the herbicidal composition and/or on the safener used and on the nature of the plant stand to be treated.

Depending on their properties, the safeners C) may be used for pretreating the seed of the crop plant (seed dressing) or incorporated into the seed furrow prior to sowing or applied together with the herbicide mix before or after emergence of the plants.

The pre-emergence treatment includes not only the treatment of the area under cultivation before sowing, but also the treatment of the areas under cultivation where seed has been sown but the plants have not yet emerged. The joint application together with the herbicide mix is preferred. To this end, tank mixes or readymixes may be employed.

The required application rates of the safeners may vary within wide limits, depending on the indication and the herbicide used, and are, as a rule, in the range of 0.001 to 1 kg, preferably 0.005 to 0.2 kg, of active substance per hectare. Particularly advantageous herbicidal compositions within the scope of the invention result when herbicides selected from the group consisting of A) are employed in combination with vegetable oils B) and the safener C1-1, C2-1 and/or C3-1.

The present invention also relates to a method of controlling undesired plants which comprises applying a herbicidally active amount of the herbicidal composition according to the invention, for example to the plants, the parts of the plants, the seeds of the plants or the area under cultivation.

In a preferred variant of the method, the compounds of the formula (I) and/or their salts are applied at application rates of 0.1 to 200 g ai/ha, preferably 0.5 to 100 g ai/ha. It is furthermore especially preferred to apply the active substances in the form of tank mixes, the individual components, for example in the form of formulations, jointly being mixed in the tank with water and the resulting spray mixture being applied. Since the crop plant tolerance of the combinations according to the invention is decidedly good while simultaneously effecting very good control of the harmful plants, the combinations can be considered as selective. In a preferred modification of the method, herbicidal compositions with the active substance combinations according to the invention are therefore employed for the selective control of undesired plants.

The herbicidal compositions can be applied in the customary manner, for example with water as carrier in amounts of approximately 100 to 1000 liters of spray mixture/ha. The compositions may also be applied by the low-volume and ultra-low-volume methods (ULV) and in the form of granules and microgranules.

The herbicidal combinations according to the invention can be employed advantageously for controlling undesired plants, also in transgenic crops. Transgenic crops are those in which the plants have been made resistant to herbicides or pesticides by means of genetic manipulation. Crop plants modified thus then allow a selective use.

In total, the invention therefore also relates to the use of herbicidal compositions comprising A) one or more sulfonylureas of the formula (I) and/or their salts

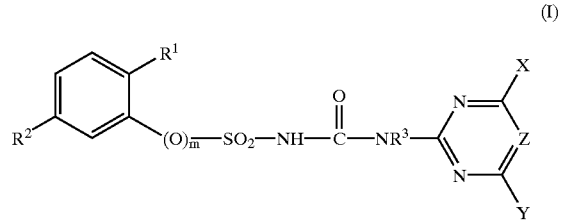

(I)

in which

R$^1$ is C$_2$–C$_4$-alkoxy or CO—R$^a$, where R$^a$ equals OH, C$_1$–C$_4$-alkoxy or NR$^b$R$^c$, in which R$^b$ and R$^c$ independently of one another are identical or different and are H or C$_1$–C$_4$-alkyl, R$^2$ is halogen or (A)$_n$—NR$^d$R$^e$, in which n equals zero or 1, A is a group CR'R", in which R' and R"

independently of one another are identical or different and are H or $C_1-C_4$-alkyl, $R^d$ equals H or $C_1-C_4$-alkyl and $R^e$ is an acyl radical and, in the event that $R^1$ equals $C_2-C_4$-alkoxy, $R^e$ may also be H, $R^3$ is H or $C_1-C_4$-alkyl, m equals zero or 1, X and Y independently of one another are identical or different and are $C_1-C_6$-alkyl, $C_1-C_6$-alkoxy or $C_1-C_6$-alkylthio, each of the three radicals mentioned being unsubstituted or substituted by one or more radicals selected from the group consisting of halogen, $C_1-C_4$-alkoxy and $C_1-C_4$-alkylthio, or are $C_3-C_6$-cycloalkyl, $C_2-C_6$-alkenyl, $C_2-C_6$-alkynyl, $C_3-C_6$-alkenyloxy or $C_3-C_6$-alkynyloxy, preferably $C_1-C_4$-alkyl or $C_1-C_4$-alkoxy, Z equals CH or N, and B) one or more vegetable oils for controlling undesired harmful plants, preferably in crops.

Crops in which the herbicidal compositions according to the invention can be employed and which may be mentioned are, for example, cereals (wheat, rye, oats, barley), maize, rice, sorghum and millet, soy beans, oil seed rape, sunflowers and cotton.

A preferred use relates to the application of herbicidal compositions which comprise A and B components in a synergistically active amount.

The invention also extends to mixtures of one or more components A), preferably A8, A9, A10, A11, A13, A15 and/or A16, and one or more components B), if appropriate in combination with one or more safeners C).

Preferred examples which may be mentioned of the herbicidal compositions according to the invention are the following combinations of A8, A9, A10, A11, A13, A15 and A16 with vegetable oils, without this being intended to constitute a restriction to the combinations mentioned explicitly:

A8+Actirob B, A8+Hasten, A8+Mero, A8+Rako-Binol,
A9+Actirob B, A9+Hasten, A9+Mero, A9+Rako-Binol,
A10+Actirob B, A10+Hasten, A10+Mero, A10+Rako-Binol,
A11+Actirob B, A11+Hasten, A11+Mero, A11+Rako-Binol,
A13+Actirob B, A13+Hasten, A13+Mero, A13+Rako-Binol,
A15+Actirob B, A15+Hasten, A15+Mero, A15+Rako-Binol,
A16+Actirob B, A16+Hasten, A16+Mero, A16+Rako-Binol,
A8+A15+Actirob B, A8+A15+Hasten, A8+A15+Mero, A8+A15+Rako-Binol,
A9+A15+Actirob B, A9+A15+Hasten, A9+A15+Mero, A9+A15+Rako-Binol,
A8+A16+Actirob B, A8+A16+Hasten, A8+A16+Mero, A8+A16+Rako-Binol.
A9+A16+Actirob B, A9+A16+Hasten, A9+A16+Mero, A9+A16+Rako-Binol.

The mixtures according to the invention can be employed expediently together with one or more safeners. Examples of preferred safeners are ethyl 1-(2,4-dichlorophenyl)-5-(ethoxycarbonyl)-5-methyl-2-pyrazoline-3-carboxylate (C1-1), 1-methylhex-1-yl 5-chloro-8-quinolinoxyacetate ($C_2$-1) and methyl 5,5-diphenyl-2-isoxazoline-3-carboxylate ($C_3$-1).

In the combinations mentioned, the use of the safeners may be advantageous since it allows potential damage to the crop plant, which may be the result of the action of sulfonylurea derivates or other herbicidally active ingredients, to be reduced.

Furthermore, the safeners C1-1, C2-1 and C3-1 can advantageously be replaced by one or more compounds selected from the following group of safeners or employed together with one or more of the following compounds:

ethyl 1-(2,4-dichlorophenyl)-5-methylpyrazole-3-carboxylate (C1-2),
ethyl 1-(2,4-dichlorophenyl)-5-isopropylpyrazole-3-carboxylate (C1-3),
1-(2,4-dichlorophenyl)-5-(1,1-dimethylethyl)pyrazole-3-carboxylate (C1-4),
ethyl 1-(2,4-dichlorophenyl)-5-phenylpyrazole-3-carboxylate (C1-5),
ethyl 1-(2,4-dichlorophenyl)-5-trichloromethyl-(1H)-1,2,4-triazole-3-carboxylate (C1-6, fenchlorazole)
ethyl 5-(2,4-dichlorobenzyl)2-isoxazoline-3-carboxylate (C1-7),
ethyl 5-phenyl-2-isoxazoline-3-carboxylate (C1-8),
1,3-dimethylbut-1-yl 5-chloro-8-quinolinoxyacetate (C2-2),
4-allyloxybutyl 5-chloro-8-quinolinoxyacetate (C2-3),
1-allyloxyprop-2-yl 5-chloro-8-quinolinoxyacetate (C2-4),
ethyl 5-chloro-8-quinolinoxyacetate (C2-5),
methyl 5-chloro-8-quinolinoxyacetate (C2-6),
allyl 5-chloro-8-quinolinoxyacetate (C2-7),
2-(2-propylideneiminooxy)-1-ethyl 5-chloro-8-quinolinoxyacetate (C2-8),
2-oxoprop-1-yl 5-chloro-8-quinolinoxyacetate (C2-9),
diethyl (5-chloro-8-quinolinoxy)malonate,
diallyl (5-chloro-8-quinolinoxy)malonate,
methyl ethyl (5-chloro-8-quinolinoxy)malonate,
2,4-dichlorophenoxyacetic acid (and its esters) (2,4-D),
4-chloro-2-methylphenoxypropionic ester (Mecoprop), MCPA,
3,6-dichloro-2-methoxybenzoic acid (and its esters) (Dicamba).

Preferred mixtures are:
A8+Actirob B+C3-1, A8+Hasten+C3-1, A8+Mero+C3-1, A8+Pako-Binol+C3-1,
A9+Actirob B+C3-1, A9+Hasten+C3-1, A9+Mero+C3-1, A9+Rako-Binol+C3-1,
A10+Actirob B+C3-1, A10+Hasten+C3-1, A10+Mero+C3-1, A10+Rako-Binol+C3-1,
A11+Actirob B+C3-1, A11+Hasten+C3-1, A11+Mero+C3-1, A11+Rako-Binol+C3-1,
A13+Actirob B+C3-1, A13+Hasten+C3-1, A13+Mero+C3-1, A13+Rako-Binol+C3-1,
A15+Actirob B+C3-1, A15+Hasten+C3-1, A15+Mero+C3-1, A15+Rako-Binol+C3-1,
A16+Actirob B+C3-1, A16+Hasten+C3-1, A16+Mero+C3-1, A16+Rako-Binol+C3-1,
A8+A15+Actirob B+C3-1, A8+A15+Hasten+C3-1, A8+A15-Mero+C3-1, A8+A15+Rako-Binol+C3-1,
A8+A16+Actirob B+C3-1, A8+A16+Hasten+C3-1, A8+A16+Mero+C3-1, A8+A16+Rako-Binol+C3-1,
A9+A15+Actirob B+C3-1, A9+A15+Hasten+C3-1, A9+A15+Mero+C3-1, A9+A15+Rako-Binol+C3-1,
A9+A16+Actirob B+C3-1, A9+A16+Hasten+C3-1, A9+A16+Mero+C3-1, A9+A16+Rako-Binol+C3-1.

A8+Actirob B+C1-1, A8+Hasten+C1-1, A8+Mero+C1-1, A8+Rako-Binol+C1-1,

A9+Actirob B+C1-1, A9+Hasten+C1-1, A9+Mero+C1-1, A9+Rako-Binol+C1-1,

A10+Actirob B+C1-1, A10+Hasten+C1-1, A10+Mero+C1-1, A10+Rako-Binol+C1-1,

A11+Actirob B+C1-1, A11+Hasten+C1-1, A11+Mero+C1-1, A11+Rako-Binol+C1-1,

A13+Actirob B+C1-1, A13+Hasten+C1-1, A13+Mero+C1-1, A13+Rako-Binol+C1-1,

A15+Actirob B+C1-1, A15+Hasten+C1-1, A15+Mero+C1-1, A15+Rako-Binol+C1-1,

A16+Actirob B+C1-1, A16+Hasten+C1-1, A16+Mero+C1-1, A16+Rako-Binol+C1-1,

A8+A15+Actirob B+C1-1, A8+A15+Hasten+C1-1, A8+A15+Mero+C1-1, A8+A15+Rako-Binol+C1-1, A8+A16+Actirob B+C1-1, A8+A16+Hasten+C1-1, A8+A16+Mero+C1-1, A8+A16+Rako-Binol+C1-1, A9+A15+Actirob B+C1-1, A9+A15+Hasten+C1-1, A9+A15+Mero+C1-1, A9+A15+Rako-Binol+C1-1, A9+A16+Actirob B+C1-1, A9+A16+Hasten+C1-1, A9+A16+Mero+C1-1, A9+A16+Rako-Binol+C1-1.

In addition, the herbicidal compositions according to the invention may also comprise one, two or more of agrochemicals other than component A (for example herbicides, insecticides, fungicides and the like) to complete the spectrum of properties, usually in minor amounts.

This allows a large number of possibilities of combining a plurality of active substances with each other and to employ them jointly for controlling harmful plants in crops without deviating from the spirit of the invention.

The herbicidal compositions according to the invention have an outstanding herbicidal activity against a broad spectrum of economically important monocotyledonous and dicotyledonous harmful plants. The active substances also act efficiently on perennial weeds which are difficult to control and produce shoots from seeds or rhizomes, root stocks or other perennial organs. In this context, it is immaterial whether the herbicidal compositions are applied pre-sowing, pre-emergence or post-emergence.

For example, the herbicidal compositions according to the invention can be used for controlling the following harmful plants:

Dicotyledonous weeds from the genera Sinapis, Galium, Stellaria, Matricaria, Galinsoga, Chenopodium, Brassica, Urtica, Senecio, Amaranthus, Portulaca, Xanthium, Convolvulus, Ipomoea, Polygonum, Sesbania, Cirsium, Carduus, Sonchus, Solanum, Lamium, Veronica, Abutilon, Datura, Viola, Monochoria, Commelina, Sphenoclea, Aeschynomene, Heteranthera, Papaver, Euphorbia and Bidens.

Monocotyledonous weeds from the genera Avena, Alopecurus, Echinochloa, Setaria, Panicum, Digitaria, Poa, Eleusine, Brachiaria, Lolium, Bromus, Cyperus, Elytrigia, Sorghum, Apera and Scirpus.

If the herbicidal compositions according to the invention are applied before germination, then the weed seedlings are either prevented completely from emerging, or the weeds grow until they have reached the cotyledon stage, but then their growth stops and, eventually, after three to four weeks have elapsed, they die completely.

If the herbicidal compositions of the invention are applied to the green parts of the plants, growth likewise stops drastically a very short time after post-emergence treatment. The weed plants remain at the growth stage of the point of time of application, or they die more or less rapidly after a certain period has elapsed, so that in this manner competition by the weeds, which is harmful to crop plants, can be eliminated at a very early point in time and in a sustained manner, and, as a consequence, the quantitative and qualitative yield losses which this entails, can be prevented at a very early point in time and in a sustained manner by using the novel compositions according to the invention.

Although the compositions according to the invention have an outstanding herbicidal activity against monocotyledonous and dicotyledonous weeds, the crop plant is damaged not at all, or only to an negligible extent.

In summary, it can be said that the joint use of sulfonylureas of the formula (I) and/or their salts with one or more vegetable oils leads to an outstanding herbicidal effect where, in a preferred embodiment, superadditve (=synergistic) effects are found, i.e. the action in the combinations is greater than when the individual components employed are used singly.

These effects permit, inter alia, a reduction in application rate, the control of a wider spectrum of broad-leaved weeds and grass weeds, the elimination of deficiency of action, also with regard to resistant species, a more rapid and safer action, prolonged long-term action, complete control of the harmful plants with only one or few applications, and a widened period of use of the active substances in combination.

The abovementioned properties are required in weed control practice to keep agricultural crops free from undesired competing plants and thus to safeguard and/or increase the yields in terms of quality and quantity. As regards the above-described properties, the herbicidal compositions according to the invention clearly exceed the technical standard.

The examples which follow are intended to illustrate the present invention, but constitute no limitation whatsoever:

A. BIOLOGICAL EXAMPLES

Example 1

Maize was sown in spring in 6 m² plots in the open. After sowing, weeds of the species stated in Table 1 emerged in addition to the maize. After 24 days, the plots were sprayed under practice conditions with the active substance preparations at 400 l/ha (converted). The active substance preparations comprised (converted) 30 g of compound A8 in combination with 30 g of the safener C3-1 which, in the form of kaolin-based water-dispersible granules, were dispersed in 400 l of water (converted). The vegetable oils were admixed to the spray mixture by the tank mix method at the application rates stated in the table. 2 weeks after application, the action was scored in accordance with the following scheme: 100%=total destruction, 0%=no action.

The results are shown in Table 1, the action of the herbicide/safener combination and of the vegetable oil, for separate application, being stated in brackets. Thus, the harmful effect is, for example, in the case of Setaria viridis, 42% when using only the herbicide/safener combination A8+C3-1 and 0% when only using the vegetable oils.

TABLE 1

| Vegetable oil | Dosage (l/ha) | SETVI Action (%) | CHEAL Action (%) | CHEFI Action (%) | STEME Action (%) |
|---|---|---|---|---|---|
| Actirob B | 1.33 | 99 (42 + 0) | 99 (27 + 0) | 99 (25 + 0) | 100 (10 + 0) |
|  | 2.0 | 99 (42 + 0) | 99 (27 + 0) | 100 (25 + 0) | 100 (10 + 0) |
| Rako-Binol | 0.67 | 99 (42 + 0) | 91 (27 + 0) | 94 (25 + 0) | 99 (10 + 0) |
|  | 1.0 | 99 (42 + 0) | 96 (27 + 0) | 99 (25 + 0) | 100 (10 + 0) |
| Mero | 2.0 | 100 (42 + 0) | 98 (27 + 0) | 99 (25 + 0) | 100 (10 + 0) |

Abbreviations:
SETVI = *Setaria viridis*
CHEAL = *Chenopodium album*
CHEFI = *Chenopodium ficifolium*
STEME = *Stellaria media*
l/ha = liters/hectare In all cases, the example demonstrates a synergistic action of the herbicidal compositions according to the invention.

Example 2

Maize and Sorghum sudanense were sown in spring in 10 m² plots in the open. After sowing, weeds of the species stated in Table 2 emerged in addition to the species which had been sown. After 22 days, the plots were sprayed under practice conditions with the active substance preparations at 300 l/ha (converted). The active substance preparations comprised (converted) 30 g of compound A8 in combination with 30 g of the safener C3-1 which, in the form of kaolin-based water-dispersible granules, were dispersed in 300 l of water (converted). The vegetable oils were admixed to the spray mixture by the tank mix method at the application rates stated in the table. 12 days after application, the action was scored in accordance with the following scheme: 100%=total destruction, 0%=no action. The results are shown in Table 2, the action of the herbicide/safener combination and of the vegetable oil, for separate application, being stated in brackets:

TABLE 2

| Vegetable oil | Dosage (l/ha) | SORSU Action (%) | CHEAL Action (%) | ZEAMX (Maize) Action (%) |
|---|---|---|---|---|
| Actirob B | 1.33 | 98 (83 + 0) | 75 (25 + 0) | 0 |
|  | 2.0 | 98 (83 + 0) | 78 (25 + 0) | 0 |
| Rako-Binol | 0.67 | 91 (83 + 0) | 55 (25 + 0) | 0 |
|  | 1.0 | 98 (83 + 0) | 75 (25 + 0) | 0 |
| Mero | 2.0 | 100 (83 + 0) | 80 (25 + 0) | 0 |

Abbreviations
CHEAL = *Chenopodium album*
SORSU = *Sorghum sudanense*
ZEAMX = *Zea mays*
l/ha = liters/hectare The example demonstrates the synergistic action against the weeds and simultaneously the outstanding crop plant selectivity.

Example 3

Seeds or rhizome pieces of monocotyledonous and dicotyledonous harmful plants and useful plants were placed in sandy loam in pots of diameter 9 to 13 cm and covered with soil. The pots were kept in a greenhouse under optimal conditions. In the two- to three-leaf stage, i.e. approximately three weeks after cultivation has begun, the test plants were treated with the herbicides and vegetable oil in the form of aqueous dispersions or suspensions or emulsions and the green parts of the plant were sprayed with various dosage rates at an application rate of (converted) 300 l of water/ha. To grow the plants further, the pots were kept in the greenhouse under optimal conditions. The damage to the useful plants and harmful plants was evaluated visually 2–3 weeks after the treatment using the following scheme: 100%=total destruction, 0%=no action.

The test results are shown in the table hereinbelow, the action of the herbicide/safener combination and of the vegetable oil when used separately being stated in brackets:

TABLE 3

| Herbicide | | Vegetable oil | | ECHCG | SORHA | CHEAL |
|---|---|---|---|---|---|---|
| Type | Dosage kg/ha | Type | Dosage l/ha | Action (%) | Action (%) | Action (%) |
| X1 | 0.015 | Actirob B | 1 | 70 (0 + 0) | 60 (0 + 0) | 70 (0 + 0) |
| X1 | 0.015 | Hasten | 1 | 70 (0 + 0) | 60 (0 + 0) | 70 (0 + 0) |
| X1 | 0.015 | Rako-Binol | 1 | 70 (0 + 0) | 50 (0 + 0) | 75 (0 + 0) |
| X1 | 0.015 | Mero | 1 | 75 (0 + 0) | 60 (0 + 0) | 75 (0 + 0) |
| V1 | 0.015 | Actirob B | 1 | 0 (0 + 0) | 0 (0 + 0) | 0 (0 + 0) |
| V1 | 0.015 | Hasten | 1 | 15 (0 + 0) | 0 (0 + 0) | 0 (0 + 0) |
| V1 | 0.015 | Rako-Binol | 1 | 0 (0 + 0) | 0 (0 + 0) | 0 (0 + 0) |
| V1 | 0.015 | Mero | 1 | 30 (0 + 0) | 15 (0 + 0) | 0 (0 + 0) |

Abbreviations:

TABLE 3-continued

| Herbicide | | Vegetable oil | | ECHCG | SORHA | CHEAL |
|---|---|---|---|---|---|---|
| Type | Dosage kg/ha | Type | Dosage l/ha | Action (%) | Action (%) | Action (%) |

ECHCG = *Echinochloa crus galli*
SORHA = *Sorghum halepense*
CHEAL = *Chenopodium album*
X1 = A8 + C3-1
V1 = Nicosulfuron
l/ha = liters/hectare

Example 4

Rice, and Cyperus esculentus as typical harmful plant, were grown in a greenhouse under paddy rice conditions (flooding level of the water 2–3 cm) in sealed plastic pots and sprayed with an active substance preparation at an application rate of (converted) 600 l/ha. The test plants were then placed in the greenhouse under optimal growth conditions and kept like this over the entire test period. Approximately 3 weeks after the application, they were evaluated by means of visually scoring the damage to the plants in comparison with the untreated control, using the following scheme: 100%=total destruction, 0%=no action.

The test results are shown in the table hereinbelow, the action of the herbicide/safener combination and of the vegetable oil when used separately being stated in brackets:

TABLE 4

| Herbicide | | Vegetable oil | | Rice | CYPES |
|---|---|---|---|---|---|
| Active substance | Dosage kg/ha | Type | Dosage l/ha | Action (%) | Action (%) |
| A13 | 0.004 | Hasten | 1 | 0 (0 + 0) | 75 (35 + 0) |
| A13 | 0.004 | Hasten | 2 | 0 (0 + 0) | 85 (35 + 0) |

Abbreviations:
CYPES = *Cyperus esculentus*
kg/ha = kilograms/hectare

We claim:

1. A herbicidal composition comprising
A) one or more sulfonylureas of the formula (I) and/or their salts

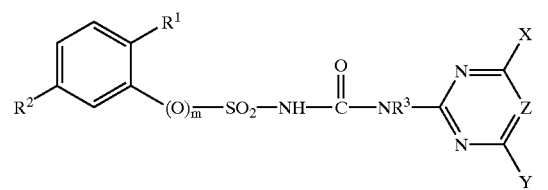

(I)

in which
$R^1$ is $C_2$–$C_4$-alkoxy or CO—$R^a$, where $R^a$ equals OH, $C_1$–$C_4$-alkoxy or $NR^bR^c$, in which $R^b$ and $R^c$ independently of one another are identical or different and are H or $C_1$–$C_4$-alkyl, $R^2$ is halogen or $(A)_n$—$NR^dR^e$, in which n equals zero or 1, A is a group CR'R", in which R' and R" independently of one another are identical or different and are H or $C_1$–$C_4$-alkyl, $R^d$ equals H or $C_1$–$C_4$-alkyl and $R^e$ is an acyl radical and, in the event that $R^1$ equals $C_2$–$C_4$-alkoxy, $R^2$ may also be H, $R^3$ is H or $C_1$–$C_4$-alkyl, m equals zero or 1, X and Y independently of one another are identical or different and are $C_1$–$C_6$-alkyl, $C_1$–$C_6$-alkoxy or $C_1$–$C_6$-alkylthio, each of the three radicals mentioned being unsubstituted or substituted by one or more radicals selected from the group consisting of halogen, $C_1$–$C_4$-alkoxy and $C_1$–$C_4$-alkylthio, or are $C_3$–$C_6$-cycloalkyl, $C_2$–$C_6$-alkenyl, $C_2$–$C_6$-alkynyl, $C_3$–$C_6$-alkenyloxy or $C_3$–$C_6$-alkynyloxy, preferably $C_1$–$C_4$-alkyl or $C_1$–$C_4$-alkoxy, Z equals CH or N, and B) one or more vegetable oils.

2. A herbicidal composition as claimed in claim 1, comprising a synergistically active content of a combination of the compounds of the formula (I) and/or their salts with vegetable oils.

3. A herbicidal composition as claimed in claim 1, additionally comprising one or more further components selected from the group consisting of agrochemical active substances of a different type, additives conventionally used in crop protection, and formulation auxiliaries.

4. A method of controlling harmful plants, wherein the herbicidal composition as defined in claim 1 is applied to the plants, parts of the plants, the seeds of the plants or the area under cultivation pre-emergence, post-emergence or pre- and post-emergence.

5. The method as claimed in claim 4 for selectively controlling harmful plants in crops.

6. A process for the preparation of a herbicidal composition as defined in claim 1, wherein the compound(s) of the formula I and/or the salts thereof (type-A compounds) is or are mixed with one or more vegetable oils.

7. The process as claimed in claim 6, wherein components A and B are mixed with water by the tank mix method.

* * * * *